US010251756B2

(12) United States Patent
Faccioli et al.

(10) Patent No.: US 10,251,756 B2
(45) Date of Patent: *Apr. 9, 2019

(54) PROSTHESIS FOR A SHOULDER ARTICULATION

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (VR) (IT)

( * ) Notice: Subject to any disclaimer, the term of this patent is extended or adjusted under 35 U.S.C. 154(b) by 35 days.

This patent is subject to a terminal disclaimer.

(21) Appl. No.: 15/520,318

(22) PCT Filed: Aug. 28, 2015

(86) PCT No.: PCT/IB2015/056538
§ 371 (c)(1),
(2) Date: Apr. 19, 2017

(87) PCT Pub. No.: WO2016/063145
PCT Pub. Date: Apr. 28, 2016

(65) Prior Publication Data
US 2017/0367835 A1 Dec. 28, 2017

(30) Foreign Application Priority Data
Oct. 21, 2014 (IT) .............. VR2014A0260

(51) Int. Cl.
*A61F 2/40* (2006.01)
*A61F 2/30* (2006.01)

(52) U.S. Cl.
CPC .............. *A61F 2/4014* (2013.01); *A61F 2/40* (2013.01); *A61F 2/4059* (2013.01); *A61F 2002/3054* (2013.01); *A61F 2002/30332* (2013.01); *A61F 2002/30354* (2013.01); *A61F 2002/30359* (2013.01); *A61F 2002/30408* (2013.01); *A61F 2002/30433* (2013.01); *A61F 2002/30436* (2013.01); *A61F 2002/30507* (2013.01); *A61F 2002/30604* (2013.01);
(Continued)

(58) Field of Classification Search
CPC ........ A61F 2/40; A61F 2/4014; A61F 2/4059; A61F 2002/4018; A61F 2002/4037; A61F 2002/4051
See application file for complete search history.

(56) References Cited

U.S. PATENT DOCUMENTS

2009/0192621 A1  7/2009  Winslow et al.
2012/0253467 A1* 10/2012 Frankle ................. A61F 2/40
                                                    623/19.11

FOREIGN PATENT DOCUMENTS

EP          1639965      3/2006
WO          2014096912   6/2014

OTHER PUBLICATIONS

International Search Report dated Nov. 12, 2015 for PCT/IB2015/056538 (2 pages).

* cited by examiner

*Primary Examiner* — Brian Dukert
(74) *Attorney, Agent, or Firm* — Tutunjian & Bitetto, P.C.

(57) ABSTRACT

Prosthesis for a shoulder joint including a humeral component equipped with a stem, a head component and connection or articulation means of the humeral component with the head component, wherein the prosthesis according to the invention can be used both as a conventional prosthesis and as a reverse-type prosthesis.

27 Claims, 9 Drawing Sheets

(52) U.S. Cl.
CPC ............... *A61F 2002/30607* (2013.01); *A61F 2002/30874* (2013.01); *A61F 2002/30878* (2013.01); *A61F 2002/4018* (2013.01); *A61F 2002/4022* (2013.01); *A61F 2002/4037* (2013.01); *A61F 2002/4051* (2013.01); *A61F 2002/4085* (2013.01)

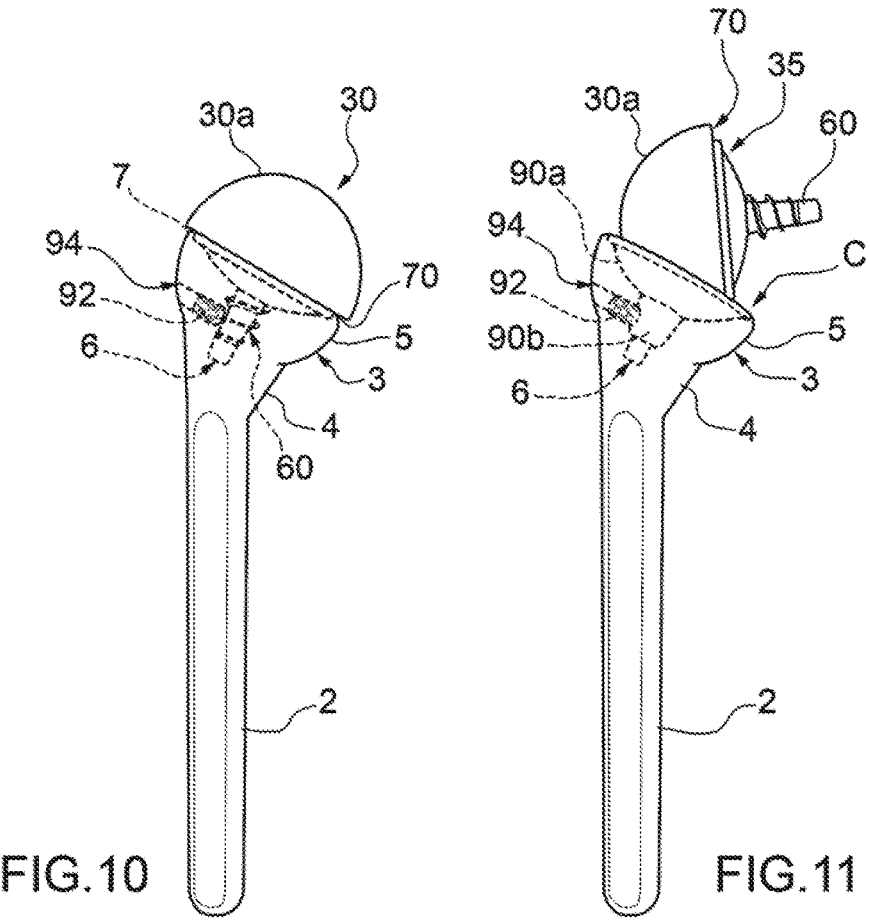
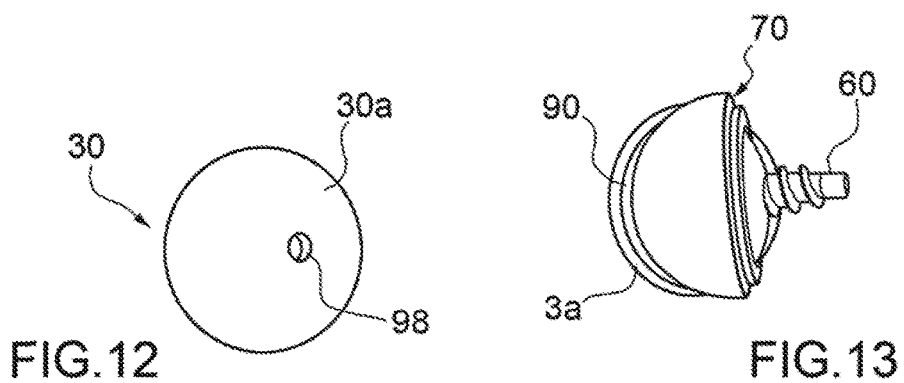

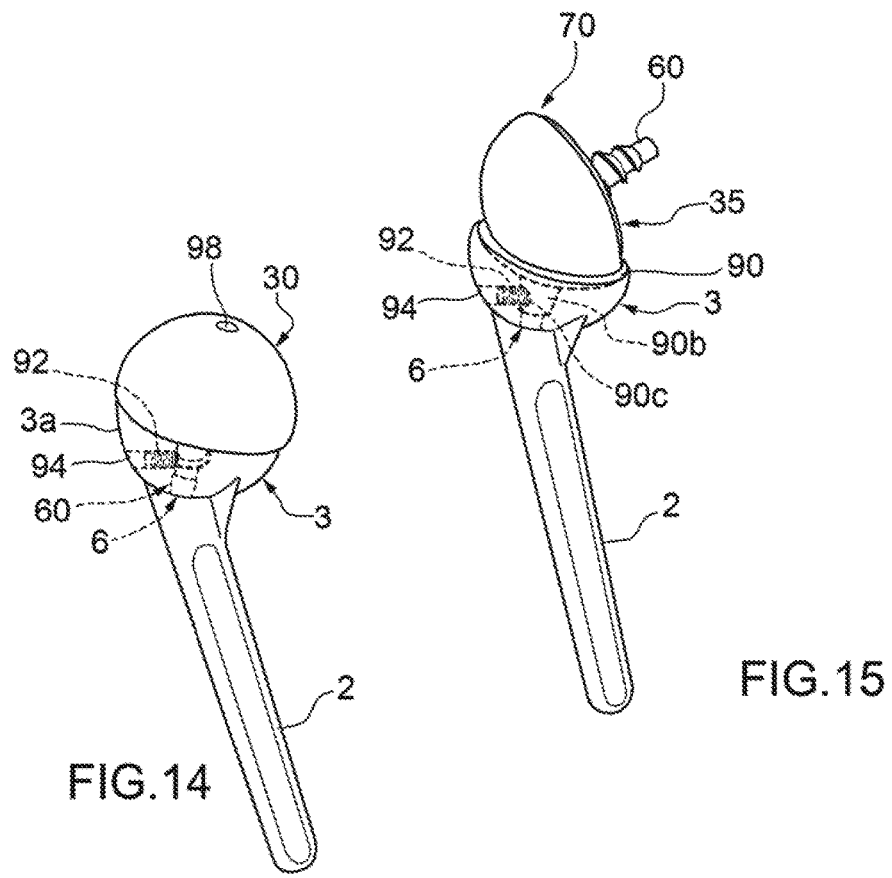
FIG.14
FIG.15
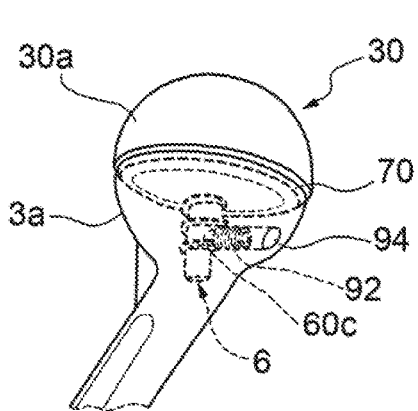
FIG.16
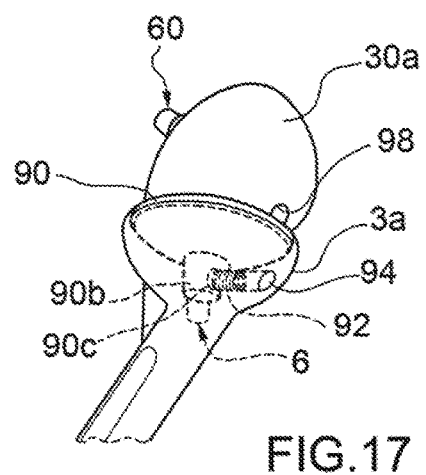
FIG.17

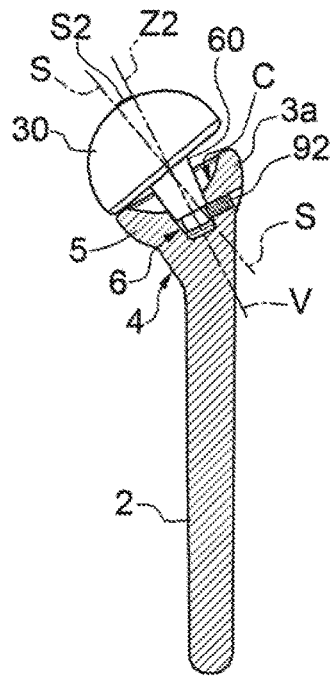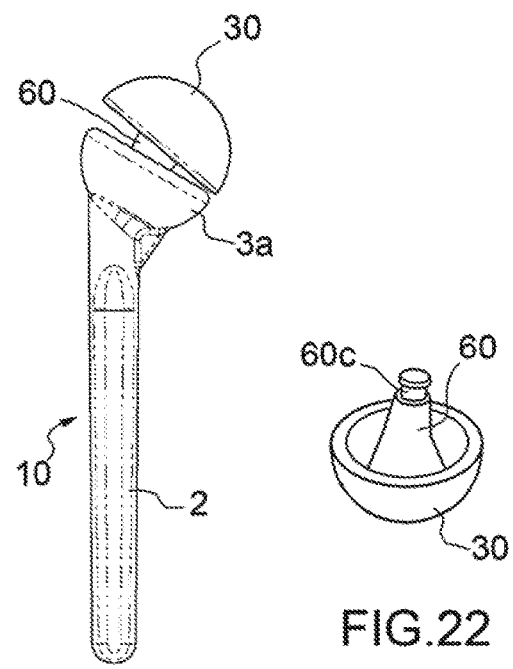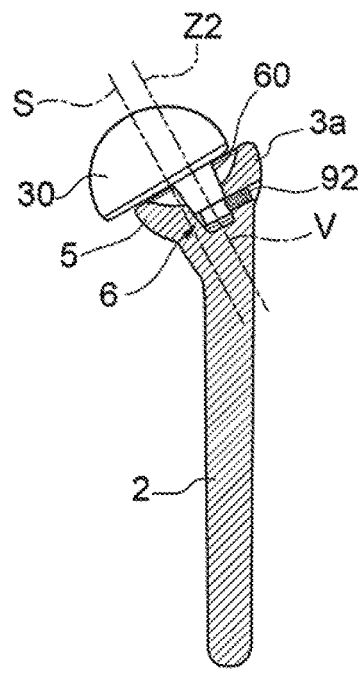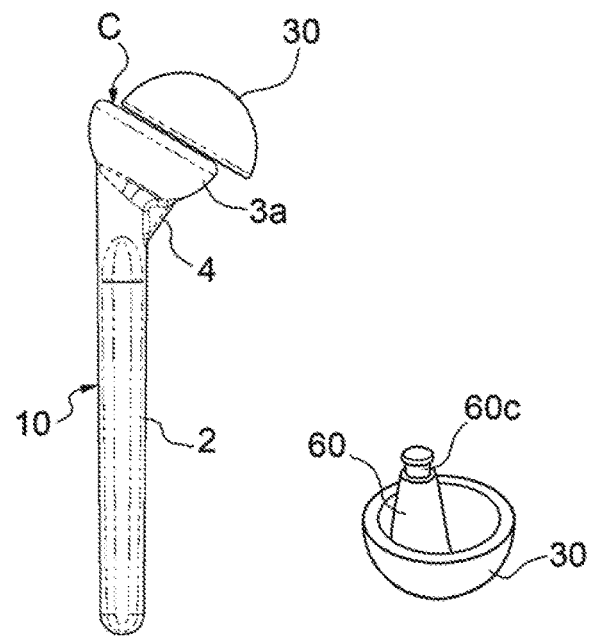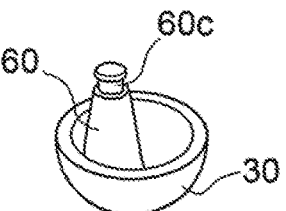
FIG.20　　　　　FIG.21　　　　　FIG.22
FIG.23　　　　　FIG.24　　　　　FIG.25

PROSTHESIS FOR A SHOULDER ARTICULATION

TECHNICAL FIELD OF THE INVENTION

The present invention regards a prosthesis for a shoulder articulation; in particular, the present invention refers to a prosthesis that can be used both as an anatomical prosthesis and as a reverse-type prosthesis.

STATE OF THE PRIOR ART

The currently-used hip prostheses are substantially of two types.

The first type is called "conventional" or "anatomical" and reproposes the normal anatomy of the shoulder joint. In particular, such a type of prosthesis foresees a humeral component constituted by a stem, to be inserted in the upper part or proximal epiphysis of the humerus, which is equipped with a hemi-spherical or semi-spherical head, which reproduces the head of the humerus and acts as a joint of the stem of the prosthesis—and thus of the humerus—with the scapula, or rather the glenoid cavity of the scapula, reforming the scapulohumeral articulation.

If the glenoid cavity is also damaged, this can be replaced by a glenoid cup or by a glenoid component, which reforms the integrity of the glenoid seat in which the head of the humeral component is articulated.

The second type of shoulder prosthesis is called "reverse" and is used when the patient, in addition to arthrosis, simultaneously suffers lesions of greater size, such as large lesions of the rotator cuff.

For these type of patients, the "conventional" (or anatomical) prosthesis of the shoulder can cause pain and limited movement, while the prosthesis of "reverse" type allows overcoming such drawbacks.

Such a second type of prosthesis provides that the glenoid component is equipped with a hemi-sphere or half-sphere, suitable for being articulated with a seat or cup obtained in the proximal end of the humeral component. Therefore, the humeral component is equipped with a cup or seat in which the head fixed to the scapula of the patient is articulated.

The "reverse" prosthesis relies on the deltoid muscle, and not on the rotator cuff that is damaged, in order to allow the movements between the shoulder and the arm. Such a type of "reverse" prosthesis, moreover, allows greater preservation of the humerus bone, which is less damaged by the operation procedure (e.g. unlike the "conventional" prosthesis, whose planting requires the resecting of the head of the humerus). In this way, the preserved bone portion can be useful if it is subsequently necessary to proceed with the implant of a further "conventional" prosthesis. Therefore, there is a need to provide a "universal" prosthesis that can be assembled, at the surgeon's discretion, both as "conventional" prosthesis and as "reverse" prosthesis.

The application n. US2009192621 discloses an implant assembly, for selectively performing reverse and traditional arthroplasty for a shoulder joint. The implant assembly includes several single pieces including a head, a cup, a humeral stem and an adaptor.

The European application n. EP1639965 discloses a shoulder arthroplasty kit for shoulder arthroplasty that includes a stem for insertion into the humerus and a first member with a surface having a convex periphery adapted for articulation with the natural glenoid fossa. The first member is removably cooperable with the stem. The kit also includes a second member including a portion having a concave periphery. The second member is removably cooperable with the stem. The kit further includes a third member for insertion into the natural glenoid fossa, having a portion with a convex periphery. The third member is adapted for articulation with the second member.

The International application n. WO2014096912 discloses a shoulder prosthesis, provided with a humeral stem having a conical proximal female seat suitable for interchangeably housing adaptors for the standard application of the shoulder prosthesis and reverse application of the shoulder prosthesis, respectively.

SUMMARY OF THE INVENTION

One object of the present invention is to improve the state of the art.

Another object of the present invention is to provide a prosthesis that is able to act both as a "conventional" prosthesis and as a "reverse" prosthesis.

Still another object of the present invention is to devise a prosthesis that is effective, safe and cost-effective.

A further object of the present invention is to obtain a prosthesis that allows maintaining the articular functionality, ensuring that the patient has a substantially normal lifestyle.

In accordance with an aspect of the invention, a prosthesis is provided according to the present specification.

BRIEF DESCRIPTION OF THE DRAWINGS

Further characteristics and advantages of the invention will become clearer from the description of several embodiments of the present invention, illustrated by way of example in the enclosed drawings, in which:

FIG. 10 is a partially transparent perspective side view of the prosthesis for a shoulder joint in the first operative configuration according to a version of the invention;

FIG. 11 is a side view of the prosthesis of FIG. 7;

FIG. 12 is a perspective view from above of a detail of the prosthesis of FIG. 10;

FIG. 13 is a view from above of the prosthesis of FIG. 11;

FIG. 14 is a slightly rear perspective view of the prosthesis of FIG. 10;

FIG. 15 is a slightly rear perspective view of the prosthesis of FIG. 11;

FIGS. 16 and 17 are slightly rear perspective views of a detail, respectively, of the prosthesis of FIG. 10 and of FIG. 7;

FIG. 20 is a side section view of a version of the present invention;

FIG. 21 is a side view of the version according to FIG. 20;

FIG. 22 is a perspective view of a component of the prosthesis according to FIG. 21;

FIG. 23 is a side section view of a further version of the present invention;

FIG. 24 is a side view of the version according to FIG. 23;

FIG. 25 is a perspective view of a component of the prosthesis according to FIG. 23;

DETAILED DESCRIPTION OF THE INVENTION

Figure 1:
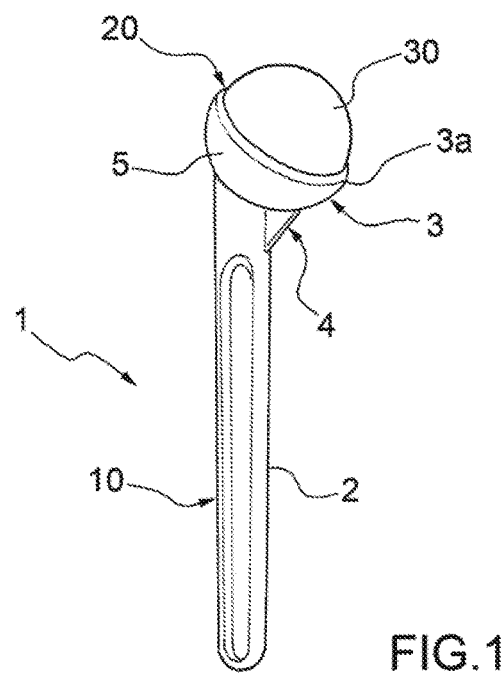
FIG. 1 is a perspective side view of a prosthesis for a shoulder joint according to the present invention in a first operative configuration.
Figure 2:
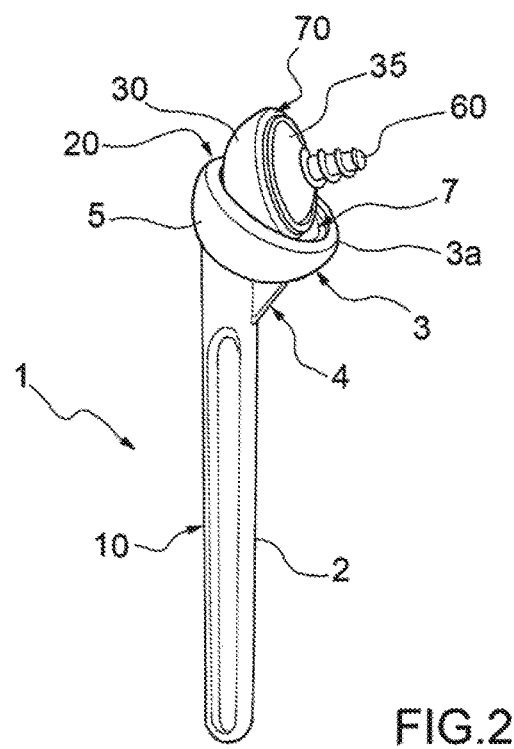
FIG. 2 is a perspective side view of a prosthesis according to the present invention in a second operative configuration.

With reference to the figures, reference number 1 indicates overall a prosthesis for a shoulder joint according to the present invention, in particular a prosthesis to be used both when during the surgical step it is necessary to use a conventional or anatomical prosthesis and a reverse one.

The prosthesis 1 is able to maintain the joint space and to ensure the articulation of the shoulder of the patient, even when there are serious lesions.

The prosthesis 1 according to the present invention is made of biologically compatible material with the tissues of the patient.

Such biologically compatible material can be selected among metals, metal alloys, organo-metallic compounds, ceramics or combinations thereof.

The prosthesis 1 can possibly comprise at least one insert 90 (which will be described better hereafter) made of plastic or polymeric material, like for example polyethylene.

In a version of the present invention, the biologically compatible material can comprise or be coated with an acrylic resin or a plastic material, a ceramic material, or a highly porous resin, or a combination thereof or a bone cement, for example polymethyl methacrylate (PMMA), or in which the aforementioned plastic or polymeric materials can be selected among thermoplastic polymers, such as acrylic resins, polyethylene, polypropylene, polyester, thermoformable polymers and other similar materials. Such a coating can cover the humeral component 10 or the stem 2 and/or the head component 30 or the portions of the prosthesis 1 most subject to rubbing.

Such a coating, when ceramic or acrylic, for example comprising hydroxyapatite, can cover the humeral component 10 or the stem 2, in the case in which it is wished to increase the osteointegration thereof with the surrounding bone tissue.

For the surfaces or the components of the prosthesis 1 most subject to wear, such coating can be made with deposition or application of metal oxides and/or nitrides, like for example titanium nitride, in order to increase the hardness thereof.

The prosthesis 1, in particular the humeral component 10 or the stem 2, besides being made from metal, in a further version of the invention can be made from a plastic or ceramic material and comprise a metallic core 80 (as can be seen for example in FIG. 3) capable of giving greater stability to the implant, high resistance to loads, etc.

The prosthesis 1 comprises a humeral component 10, a head component 30 and connection or articulation means 20 of the humeral component 10 with the head component 30. Moreover, such connection or articulation means 20 are arranged between the humeral component 10 and the head component 30.

In particular, the prosthesis 1 is formed from the aforementioned two components, in other words from the humeral component 10 and from the head component 30, which are components that are distinct and separate from one another.

In a version of the invention, the prosthesis 1 comprises only the humeral component 10 and the head component 30 and optionally an insert 90; the connection or articulation means 20 are made in a single piece or enbloc respectively in the humeral component 10 and in the head component 30 or optionally in the insert 90.

The connection or articulation means 20 connect the humeral component 10 to the head component 30 or articulate the humeral component 10 to the head component 30.

The humeral component 10 is equipped with a stem 2 and with a proximal portion 3, at its proximal end.

During use, the stem 2 is suitable for being at least partially inserted in the humeral bone while the proximal portion 3 is suitable for being directed towards the glenoid cavity of the patient.

Figure 4A:
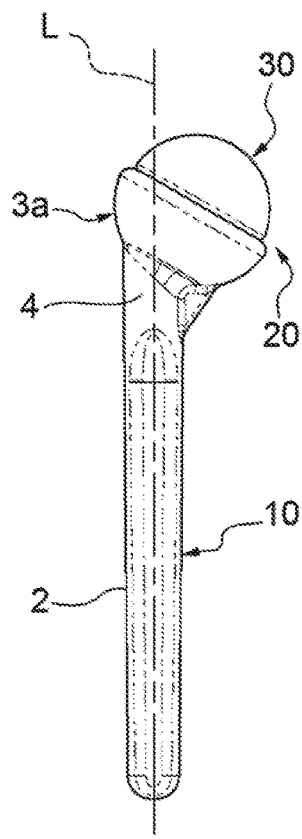
FIGS. 4A, 4B, 4C are side views of the prosthesis for a shoulder joint in the first operative configuration or anatomical configuration (FIG. 4A) and in the second operative configuration or reverse configuration (FIGS. 4B and 4C)

The stem 2 has, in one version of the invention, a cross section, taken according to a transverse plane perpendicular to the longitudinal axis L of the stem 2 (illustrated for example in FIG. 4A), that is substantially rectangular or polygonal.

The humeral component 10 comprises a joining portion 4. The joining portion 4 is positioned between the stem 2 and the proximal portion 3.

The joining portion 4 has, in one version of the invention, a cross section of greater size than the cross section of the stem 2. In such case, the joining portion 4 has "enlarged" size with respect to that of the stem 2.

The joining portion 4 determines a stiffening of the transition area between the stem 2 and the proximal portion 3 and an improved stability for the latter.

In one version of the invention, the humeral component 10 is obtained in a single piece, with the stem 2, the proximal portion 3 and the joining portion 4 stably constrained to each other.

In an alternative version, the humeral component 10 can be obtained in at least two pieces.

The proximal portion 3 has a configuration that is substantially cup-shaped 3a and/or comprises a perimeter side wall 5 which, during use, extends upward in the direction of the glenoid cavity starting from the stem 2 or better yet from the joining portion 4.

The wall 5 delimits a concave seat C.

The wall 5 has a configuration corresponding to part of the surface of a sphere, in particular it has a hemi-spherical or half-spherical or irregular configuration, whose concave seat C is facing or open towards the glenoid cavity.

In particular, the proximal portion 3, shaped like a cup 3a or hemi-spherical or semi-spherical regular, irregular or even incomplete, has a concavity or concave seat C that is hemi-spherical or semi-spherical regular, irregular or even incomplete. The concave seat C, in use, is suitable for at least partially containing or articulating with the head component 30; the concave seat C has radius ra.

The humeral component 10 or better yet the proximal portion 3 also comprises a recess or notch 6.

The recess or notch 6 extends from the concave seat C, in particular from its bottom wall, within the joining portion 4 towards the stem 2.

The connection or articulation means 20 comprise, in one version or first operative configuration, the recess or notch 6 and a protuberance 60 that extends from the head component 30.

The recess or notch 6 has a substantially cylindrical or frustoconical or nut screw configuration suitable for making a connection, stable in one version of the invention, with the head component 30, as better described hereinbelow.

Therefore, the joining portion 4 has a size or configuration "enlarged" with respect to the cross section of the stem 2 since it comprises, at its interior, the space that defines the aforesaid recess or notch 6. Therefore, the size of the joining portion 4 is greater than that of the stem 2 also in order to comprise the bulk of the recess or notch 6.

Figure 5:
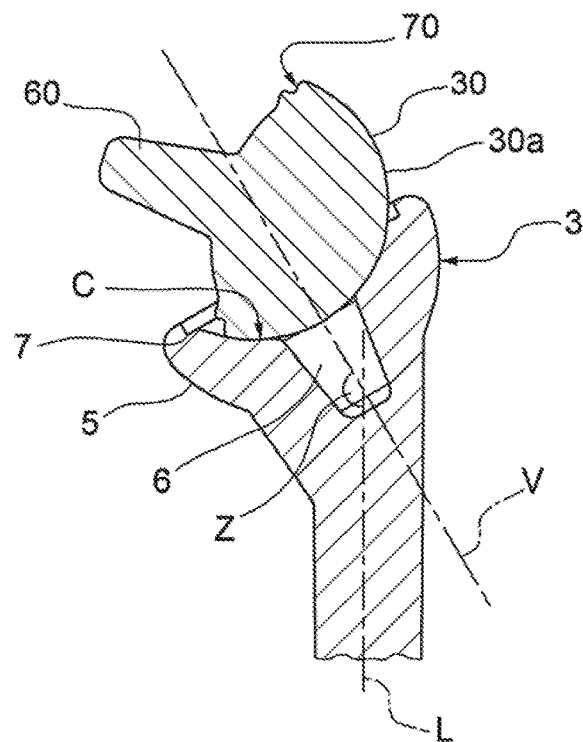
FIG. 5 is a side section view of a portion of the prosthesis in the second operative configuration.
Figure 6:
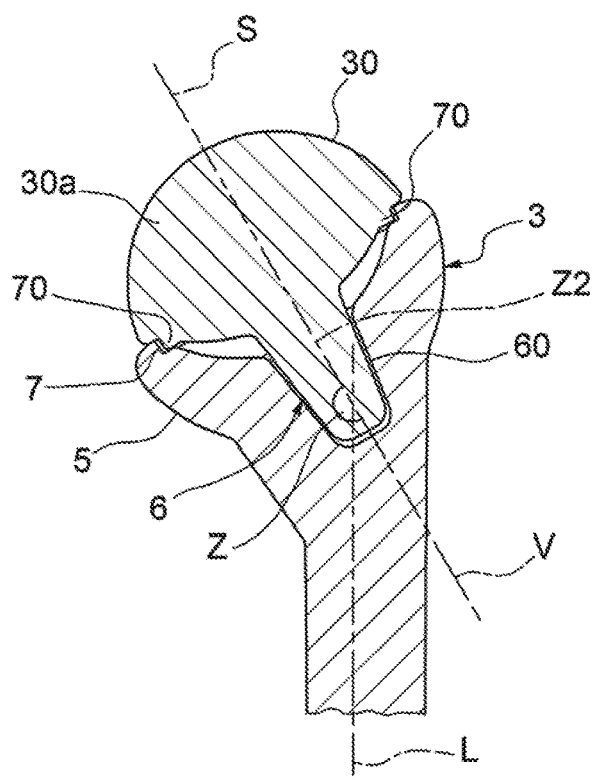
FIG. 6 is a side section view of a portion of the prosthesis in the first operative configuration.
Figure 7:
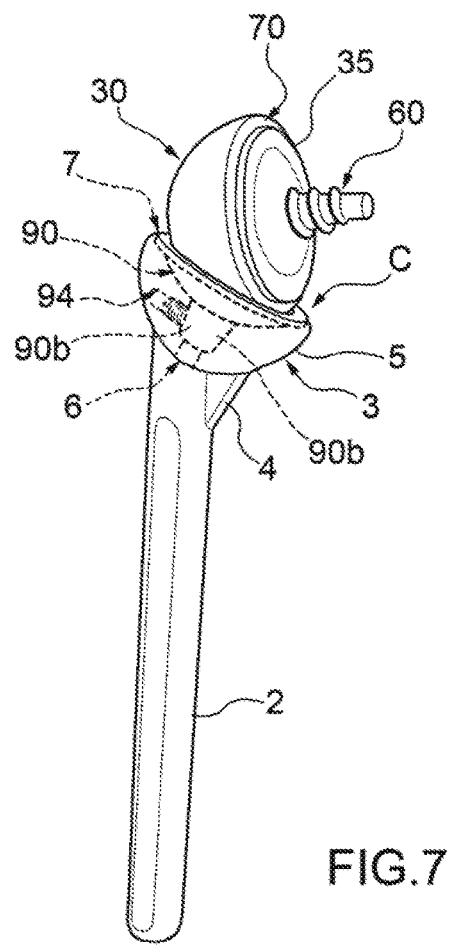
FIG. 7 is a partially transparent perspective side view of the prosthesis for a shoulder joint in the second operative configuration according to a version of the invention.
Figure 8:
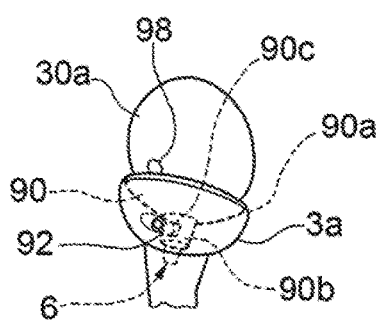
FIGS. 8 and 9 are perspective and rear views of a detail of the prosthesis of FIG. 7.
Figure 9:
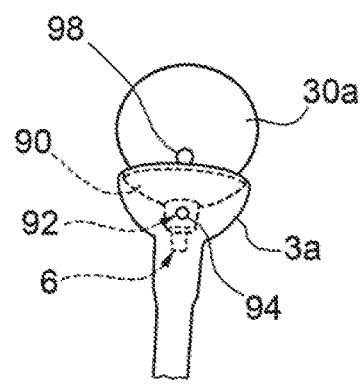
Figure 18:
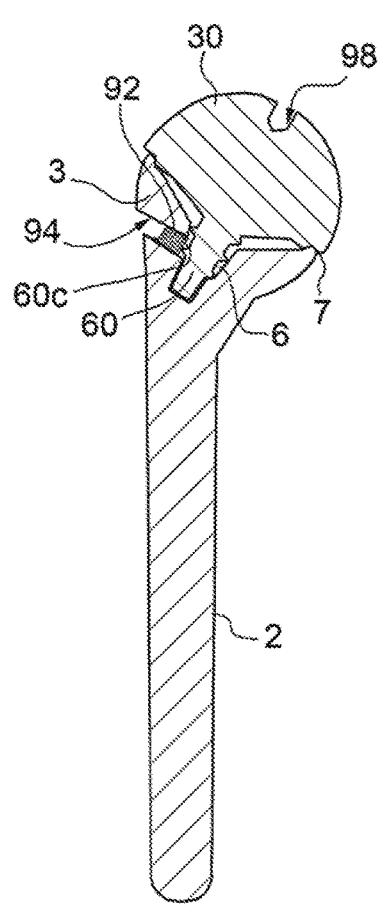
FIGS. 18 and 19 are section views corresponding to the images 10 and 11.
Figure 19:
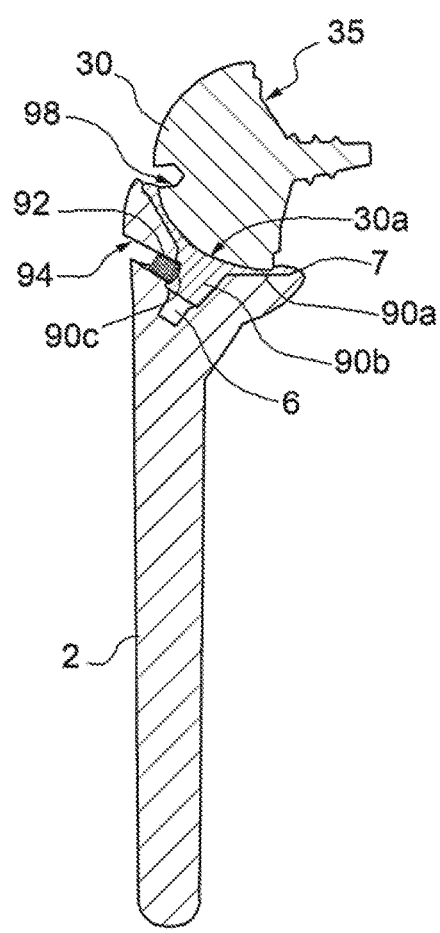

The recess or notch 6 extends inside the joining portion 4 towards the stem 2 according to an axis V (illustrated for example in FIGS. 5 and 6). The longitudinal axis L of the stem 2 and the axis V of the recess or notch 6 form an angle Z.

In one version of the invention, for example illustrated in FIG. 6, the axis V of the recess or notch 6 corresponds with the symmetry axis S of the head component 30 and with the symmetry axis Z2 of the protuberance 60.

Along the external perimeter or free peripheral edge of the wall 5 of the proximal portion 3, an annular step 7 is present. Such annular step is inside the wall 5 and hence within the concave seat C.

The prosthesis 1, as stated, further comprises a head component 30 of hemispherical or semi-spherical configuration.

The head component 30 comprises a convex surface 30a and a base 35.

In a version of the invention, the connection or articulation means 20 comprise the convex surface 30a and the concave seat C of the proximal portion of the humeral component 10, so that the surface 30a can be articulated and connected in a slidable or rotating manner with the concave seat C. In this way, the second operative configuration or reverse configuration of the prosthesis 1 according to the present invention is obtained.

In the area or surface between the base 35 and the convex surface 30a, an annular shoulder 70 is present corresponding to and matching the annular step 7 present in the proximal portion 3.

The convex surface 30a is substantially matching the concave seat C of the proximal portion 3 of the prosthesis 1.

In particular, the convex surface 30a is at least partially contained in the concave seat C, i.e. in the space or seat delimited by the wall 5 of the proximal portion 3. Therefore, the radius ra of the concave seat C is slightly greater than the radius rb of the head component 30 or better yet of its convex surface 30a.

A protuberance 60 extends perpendicularly from the base 35 towards the outside. The protuberance 60, as stated, has a substantially circular or frustoconical or frustum of pyramid shaped or screw configuration corresponding to and matching the recess or notch 6 of the proximal portion 3, or suitable for making a connection with the humeral component 3 or with the glenoid cavity of the patient.

Figure 3:
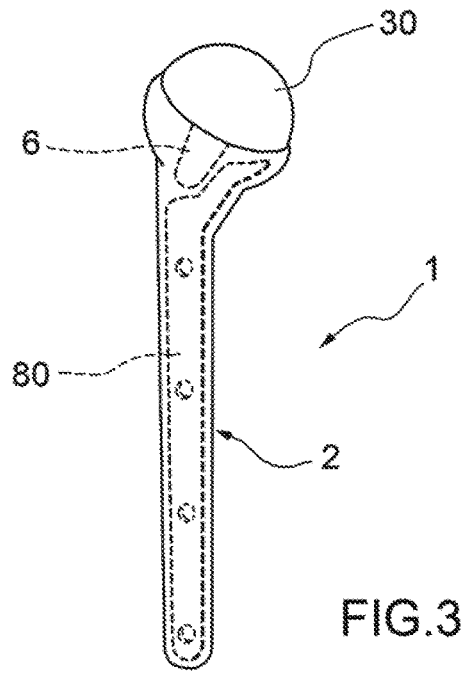
FIG. 3 is a partially transparent side view of the shoulder prosthesis according to FIGS. 1 and 2, in the first operative configuration.
Figures 4B, 4C:
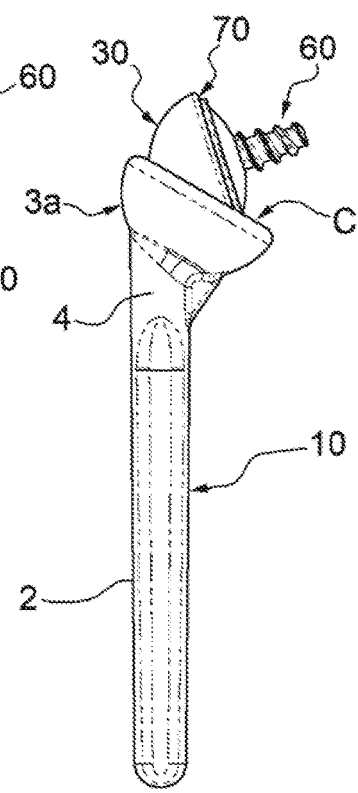

In particular, the protuberance 60 is suitable for being inserted, according to a first operative configuration, for example illustrated in FIGS. 1, 3, 4 A, 6, 10, 12, 14, 16, 18, 20-21, 23-24 and 26-28 of the drawings enclosed herein, in the recess or notch 6 of the proximal portion 3, thus making the connection between the proximal portion 3 and the stem 2 of the humeral component 10.

In such a first operative configuration, the prosthesis 1 according to the present invention can be implanted as a shoulder prosthesis of the "conventional" or "anatomical type". In this case, the humeral component 10, through the convex surface 30a of the head component 30 will articulate with the glenoid cavity of the scapula of the patient.

In a further version of the invention, for example illustrated in FIGS. 20 to 22, the axis V of the recess or notch 6 corresponds with the main symmetry axis Z2 of the protuberance 60 but does not correspond with the symmetry axis S of the head component 30. In such case, the protuberance 60 is tilted, with respect to the symmetry axis S of the head component 30, by an angle S2. Such a configuration allows angling the head component 30 with respect to the humeral component 10 in a manner so as to more correctly support the anatomy of the patient and the surgical requirements of the implant.

In a still further version of the invention, for example illustrated in FIGS. 23 to 25, the axis V of the recess or notch 6 corresponds with the symmetry axis Z2 of the protuberance 60 but these do not correspond with the symmetry axis S of the head component 30: the symmetry axis S of the head component 30, in fact, is parallel but offset with respect to the symmetry axis Z2 of the protuberance 60. In such a manner, the protuberance 60 is eccentric with respect to the center of the base 35 or of the head component 30; the head component 30 is offset with respect to the concave seat C of the proximal portion 3 of the humeral component 2 and therefore it projects laterally with respect thereto. Also this version allows more correctly supporting the anatomy of the patient and the surgical requirements of the implant. In such versions, the protuberance 60 preferably does not have a thread, such that the protuberance 60 can be inserted according to any orientation and position in the recess or notch 6 without having to rotate and hence without coming into contact or rubbing with the edges of the wall 5, which could occur if it was necessary to screw the protuberance 60.

The prosthesis 1 according to the present invention, however, can also be used in a second operative configuration, illustrated in FIGS. 2, 4B, 4C, 5, 7, 8, 9, 11, 13, 15, 17 and 19 of the enclosed drawings, when the head component 30 is inserted in the cup-shaped 3a or hemi-spherical or half-spherical configuration of the proximal portion 3, so that the convex surface 30a of the head component 30 is arranged in contact and suitable for being slidably articulated with the concave seat C of the proximal portion 3.

In this version, the protuberance 60 of the head component 30 projects externally and is suitable for being inserted in the glenoid cavity of a patient's shoulder.

In a version of the invention, in such a second operative configuration there is at least one insert 90. The insert 90, illustrated for example in FIGS. 7 to 9 and 11, 13, 15, 17 and 19, has a first cup-shaped, hemi-spherical or semi-spherical portion 90a, of analogous configuration to the concave seat C or to the cup-shaped, hemispherical or semi-spherical configuration 3a of the proximal portion 3, but of slightly smaller dimensions, so that such an insert 90 is contained in the concave seat C or in the cup-shaped, hemi-spherical or semi-spherical configuration 3a of the proximal portion 3.

The first portion 90a, in its outer peripheral portion, has a shoulder totally analogous to the annular shoulder 70 of the head portion 3, corresponding to and matching the annular step 7 present in the proximal portion 3 of the humeral component 10. In this way, when inserted in the concave seat C, the shoulder of the first portion 90a abuts against the annular step 7 of the proximal portion 3 of the humeral component 10.

In a version of the invention, the insert 90 is pressure inserted in the concave seat C or in the cup-shaped, hemispherical or semi-spherical configuration 3a of the proximal portion 3.

In this way, the convex surface 30a of the head component 30 is placed in contact and suitable for being slidably articulated with the insert 90—or with its first portion 90a—inserted in the concave seat C of the proximal portion 3.

As stated, such at least one insert 90 is made from plastic or polymeric material, like for example polyethylene, polypropylene, polyester, and other similar materials. In particular, the at least one insert 90 is made from a material capable of reducing the friction between the convex surface 30a of the head component 30 and the concave seat C, so as to increase the sliding ability of such components. In a version of the invention, the at least one insert 90 is made from ultra-high molecular weight polyethylene (UHMWPE) that acts as a bearing between the head component 30 and the proximal portion 3 of the humeral component, in the second operative configuration of the present invention.

Such at least one insert 90 has a second projecting portion 90b at the bottom of the portion 90a defined above having a substantially cup-shaped configuration.

Such a second projecting or tang portion 90b has a substantially frustoconical or frustum of pyramid shaped configuration or in any case a configuration corresponding to the configuration of the recess or notch 6 in which it is inserted. The second projecting or tang portion 90b also has a recessed seat 90c, arranged on the side surface of the second portion 90b, the function of which will be defined better hereafter.

Moreover, the prosthesis 1 comprises at least one dowel 92.

Such a dowel can be inserted through a suitable opening 94 made in the side surface of the humeral component 10, or rather in its proximal portion 3.

The opening 94 is suitable for being in communication with the recess or notch 6, in particular with the portion of the recess or notch 6 facing towards the concave seat C.

The dowel 92 is suitable for interfering with other components of the prosthesis 1, specifically with the protuberance 60 in the first operative configuration or anatomical configuration and with the second projecting or tang portion 90b of the at least one insert 90, in particular with its seat 90c.

In a version of the invention, the dowel 92 is made from a material suitable for interfering with or blocking the part or the component with which it comes into contact or has a substantially threaded bolt-type configuration.

In a version of the invention, the dowel 92 is made from a hard material, for example steel A1S1316 or metal that constitutes the stem 2 or the metallic core 80, so as to ensure the insertion thereof and the possible removal thereof by the surgeon, without the risk of ruining the interface with the locking key of the dowel itself. In a version of the invention, indeed, the dowel 92, on the opposite side with respect to that of contact with the other part or the other component of the prosthesis 1, thus in its end facing outwards, has a head able to engage with a tool actuated from the outside and suitable for slotting or screwing or stably positioning it. Vice-versa, such a tool can also be used for the removal of the dowel itself, if necessary.

The prosthesis 1 can comprise reference means (not illustrated) capable of creating a position reference between the seat 90c and the opening 94, so that the surgeon who positions the insert 90 has an easier task of aligning such an opening 94 with the seat 90c with which the dowel 92, inserted through the opening 94, will interfere.

Such reference means can be of the geometric type, for example creating a particular and unequivocal method of insertion of the second projecting or tang portion 90b in the recess or notch 6, or of the graphical type or furthermore through suitable incisions or markings present in the prosthesis 1.

The at least one insert 90 is not present in a version of the first configuration of the prosthesis 1 according to the present invention.

In the first operative configuration of the prosthesis 1, the protuberance 60 is inserted in the recess or notch 6 and the convex surface 30a of the head component 30 recreates the head of the stem 2 (and hence of the humerus of the patient) in a substantially continuous manner, coming to realize an articulation surface with the glenoid cavity of the patient itself.

In this case, the dowel 92 is inserted in the opening 94 so as to interfere, according to the ways mentioned above, with the protuberance 60, in particular with a seat 60c made for the purpose, which is firmly inserted or screwed in the recess or notch 6 and then stopped by the dowel 92.

In both configurations, the dowel 92 is substantially perpendicular to the surface with which it interferes.

The dowel 92 is therefore a fixing element of the component or of the part with which it comes into contact.

In the second operative configuration, instead, the prosthesis 1 according to the present invention can be implanted according to the type defined as "reverse". In this case, the protuberance 60 is inserted in the glenoid cavity and therefore the convex surface 30a is articulated within the concave seat C of the proximal portion, which is fixed, by means of the stem 2, to the patient's humerus.

As is visible in FIG. 6 or 10, if it is desired to use the prosthesis 1 according to the present invention according to its first operative configuration, defined as "conventional" or "anatomical", the protuberance 60 of the head component 30 is inserted in the recess or notch 6.

The protuberance 60 is blocked through the dowel 92, which is inserted through the opening 94.

Thereafter, in a version of the invention, the annular step 7 of the proximal portion 3 is brought into contact with or abutment against the annular shoulder 70 of the head component 30, and possibly the whole thing is fixed through bone cement or an adhesive component suitable for such purpose.

In an alternative version of the invention, the step 7 and the respective annular shoulder 70 can be absent.

In this way, the convex surface 30a is arranged for being articulated and coming into contact with the glenoid cavity of the patient's scapula.

As is visible in FIG. 5 or 11, however, if it is desired to use the prosthesis 1 according to the present invention according to its second operative configuration, defined as "reverse", the convex surface 30a of the head component 30 is placed in contact with or abutted against the internal surface of the concave seat C of the proximal portion 3, i.e. the head component 30 is inserted, with its convex surface 30a facing towards the stem 2, in the cup-shaped 3a or hemi-spherical or half-spherical configuration of the proximal portion 3 or in the first portion 90a of the at least one insert 90.

The convex surface 30a is thus rotated and oriented in the concave seat C until the protuberance 60 has the desired inclination so that it can be inserted in the bone of the glenoid cavity of the patient and therefore the convex surface 30a of the head component 30, which is constrained to the glenoid cavity for example through bone cement or other suitable adhesive means, is arranged for being articulated and coming into contact with the concave seat C of the proximal portion 3 of the prosthesis 1 or with the at least one insert 90, such a proximal portion 3 in turn being constrained, through the stem 2, to the patient's humerus.

When the at least one insert 90 is present, the surgeon inserts it and positions it in the concave seat C of the proximal portion 3 of the humeral component 10, its second projecting or tang portion 90b is inserted in the recess or notch 6, if necessary the second projecting or tang portion 90b is oriented so that the seat 90c is at the opening 94, the dowel 92 is inserted in the opening 94 and, through it, the at least one insert 90 is fixed to the proximal portion 3 of the humeral component 10, in particular to the concave seat C.

The protuberance 60 can be configured as a Morse taper (e.g. illustrated in FIG. 4B), suitable for being fit in the recess or notch 6 of the proximal portion 3.

In an alternative version of the invention, the protuberance 60 can have a thread (e.g. illustrated in FIG. 10) suitable for being screwed to a corresponding nut screw provided in the internal surface of the recess or notch 6 (nut screw not illustrated). In a version of the invention, the seat 60c can have a circular throat configuration, suitable for receiving the tip or end of the dowel 92.

Figure 26:
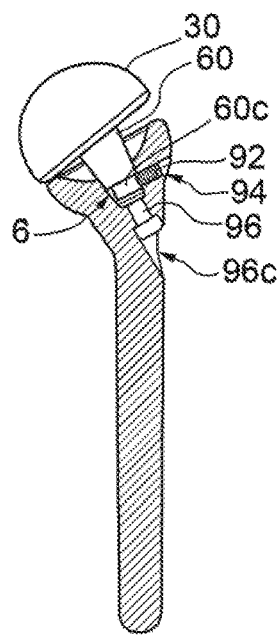
FIG. 26 is a side section view of a further version of the present invention.
Figures 27, 28, 29:
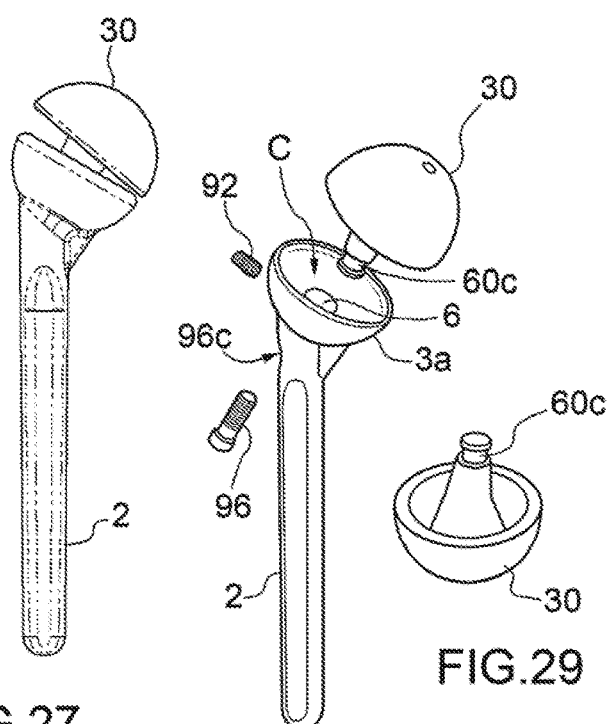
FIG. 27 is a side view of the version according to FIG. 26.
FIG. 28 is an exploded perspective view of the version according to FIG. 27.
FIG. 29 is a perspective view of a component of the prosthesis according to FIG. 27.

In a further version of the invention, in addition to the dowel 92 (as illustrated in FIGS. 26-28), or as an alternative to it (version not illustrated) there is a lock screw or Allen screw 96 and a seat 96c for the entry of the lock screw or Allen screw 96. The seat 96c is an opening arranged at the side of the stem and allows the lock screw or Allen screw 96, once inserted in the seat 96c itself, to stably engage or fix as a tie rod the end of the protuberance 60, inserted in the recess or notch 6 of the prosthesis 1.

Such a lock screw or Allen screw 96, in addition to or instead of the dowel 92, makes it possible to stably fix and keep in position over time, the head component 30 in the humeral component 10, once the surgeon has established that such an "anatomical" configuration of the prosthesis 1 is necessary for the specific requirements of the patient. In a further version of the invention, the lock screw or Allen screw 96 engages with and locks the recessed seat 90c present in the second projecting or tang portion 90b of the at least one insert 90 according to the second operative configuration of the prosthesis 1.

In a still further version of the invention, the protuberance 60 can have a thread or a Morse taper configuration in order to be screwed or fittingly locked in the glenoid cavity of the patient, according to the second operative configuration of the prosthesis 1 according to the present invention.

In order to improve the stability of the implant, the load resistance and to therefore ensure a good quality of life to the patient, the prosthesis 1, in particular the stem 2 and/or the joining portion 4, have a reinforcing core 80, inserted inside the stem 2 and/or the joining portion 4.

In particular, such a reinforcing core 80 can be metallic, when the biologically compatible material that composes the prosthesis 1 is a non-metallic material or when it is needed.

It is thus seen that the prosthesis 1 according to the present invention attains the provided objects. In particular, the doctor is able to use a single prosthesis, both in situations that require the implantation of a shoulder prosthesis of "conventional" type, and of that of "reverse" type. Hence, with regard to maintaining both possibilities open, the magazine spaces for storing such prosthesis and also the costs are considerably reduced, since it is sufficient to have a single model of prosthesis, for both operation types. In addition, in the case of implantation of the reverse prosthesis, it is possible to adjust the insertion angle of the head component 30 on the glenoid cavity of the patient, in a manner so as to render such insertion more adhering to the anatomy or to the operational needs of the patient itself.

In a version of the invention, the head component 30 has, on its top, on the opposite side with respect to its base 35, a slot 98 for a tool, so that its insertion or its screwing into the recess or notch 6 or in the bone of the patient can be made easier.

The present invention thus conceived is susceptible of numerous modifications and variations, all falling within the protective scope of the claims.

In particular, characteristics described for one version of the invention can also be combined with other versions, without departing from the protective scope of the following claims.

The invention claimed is:

1. A prosthesis for a shoulder joint, comprising a humeral component equipped with a stem,
    wherein said humeral component comprises a proximal portion, wherein said stem is suitable for being inserted in use in the humerus of a patient,
    and wherein said proximal portion is suitable for facing in use towards the glenoid cavity of the patient's shoulder,
    wherein said humeral component comprises a joining portion positioned between said stem and said proximal portion,
    wherein said prosthesis comprises a head component and connection or articulation means of said humeral component with said head component, said connection or articulation means comprising a protuberance and a recess or notch,
    wherein said humeral component comprises a single piece comprised of said stem, said proximal portion and said joining portion stably constrained to each other,
    wherein said proximal portion comprises a concave seat (C), wherein said concave seat has a configuration substantially cup-shaped, or hemispherical or half-spherical regular, irregular or incomplete, wherein said recess or notch is formed within the joining portion and extends from a bottom of the concave seat towards said stem,
    wherein said proximal portion comprises a side or perimeter wall that defines said concave seat (C),
    wherein said concave seat, during use, is suitable for at least partially containing said head component or articulating with said convex articulating surface of said head component,
    wherein said protuberance is configured to be disposed in the recess or notch formed in said concave seat within the joining portion towards said stem or configured to connect the glenoid cavity of the patient, and
    whereby said prosthesis can be used both as an anatomical prosthesis and as a reverse-type prosthesis.

2. The prosthesis according to claim 1, wherein said connection or articulation means are arranged between said humeral component and said head component.

3. The prosthesis according to claim 1, wherein said concave seat (C) is suitable for at least partially containing at least one insert suitable for articulating with said head component, wherein said at least one insert has a first portion that is cup-shaped, or hemi-sphere-shaped or half-sphere shaped regular, irregular or even incomplete.

4. The prosthesis according to claim 3, wherein said head component has a hemi-spherical or semi-spherical configuration and/or wherein said head component comprises a convex surface, an axis of symmetry (S) and a base and/or wherein said convex surface has a hemispherical or semi-spherical configuration substantially matching the configuration of said concave seat (C) or of said at least one insert.

5. The prosthesis according to claim 4, wherein said connection or articulation means comprise said convex surface and said concave seat (C) of said proximal portion of said humeral component or comprise said convex surface and said at least one insert, according to a second operative configuration or reverse configuration of the prosthesis.

6. The prosthesis according to claim 1, wherein said recess or notch extends according to a longitudinal axis (V) from said concave seat (C) of said humeral component, and the protuberance that extends according to an axis of symmetry (Z2) from said head component, according to a first operative configuration or anatomical configuration of the prosthesis, wherein said longitudinal axis (V) corresponds to said axis of symmetry (Z2) and wherein said axis of symmetry (Z2) corresponds with the axis of symmetry (S) of the head component or it is parallel and offset with respect to said axis of symmetry (S) of the head component or it makes an angle (S2) with said axis of symmetry (S) of the head component.

7. The prosthesis according to claim 6, wherein said recess or notch extends inside said joining portion or inside said proximal portion of said humeral component or wherein said recess or notch has a configuration substantially cylindrical, or frustoconical, or frustum of pyramid shaped or of nut screw or a configuration suitable for making a connection with said head component.

8. The prosthesis according to claim 4, wherein said head component comprises said protuberance that extends perpendicularly from said base.

9. The prosthesis according to claim 6, wherein said protuberance has a configuration substantially cylindrical, or frustoconical, or frustum of pyramid shaped or of screw type or a configuration suitable for making a connection with said humeral component, according to said first operative configuration or anatomical configuration of the prosthesis or with the glenoid cavity of the patient according to said second operative configuration or reverse configuration of the prosthesis.

10. The prosthesis according to claim 6, wherein said protuberance is suitable for being inserted, during use, in said recess or notch of said humeral component, according to said first operative configuration or anatomical configuration of the prosthesis.

11. The prosthesis according to claim 4, wherein said convex surface is inserted in said concave seat (C) or in said at least one insert and articulates with it, according to said second operative configuration or reverse configuration of the prosthesis.

12. The prosthesis according to claim 1, wherein said proximal portion comprises an annular step arranged at the free peripheral edge or outer perimeter of said wall.

13. The prosthesis device according to claim 12, wherein between said base and said convex surface there is an annular shoulder corresponding to and matching said annular step of said proximal portion or wherein said first portion of said at least one insert has an annular shoulder corresponding to and matching said annular step of said proximal portion.

14. The prosthesis according to claim 1, comprising a reinforcing inner core.

15. The prosthesis according to claim 1, comprising a biologically compatible material selected among: metals, metallic alloys, organo-metallic compounds, ceramics or combinations thereof, or wherein said biologically compatible material comprises or is coated with an acrylic resin or a plastic material, a ceramic material, or a highly porous resin, and/or a combination thereof or a bone cement, polymethyl methacrylate (PMMA).

16. The prosthesis according to claim 3, wherein said at least one insert is made from at least one among plastic or polymeric materials selected from thermoplastic polymers, acrylic resins, polyethylene, polypropylene, polyester, thermoformable polymers, ultra-high molecular weight polyethylene (UH WPE) or other similar materials.

17. The prosthesis according to claim 1, wherein said humeral component and said head component can be arranged in said first operative configuration to form a conventional or anatomical shoulder prosthesis, as well as in said second operative configuration to form a reverse shoulder prosthesis.

18. The prosthesis according to claim 6, wherein in said first operative configuration, said protuberance is inserted in said recess or notch, thus making the connection between said head component and said humeral component.

19. The prosthesis according to claim 5, wherein in said second operative configuration said head component is inserted in said cup-shaped or hemispherical or semi-sphcrical configuration or in said at least one insert, so that the convex surface of said head component is placed in contact and suitable for being slidably articulated with said concave seat (C) of said proximal portion or with said at least one insert.

20. The prosthesis according to claim 6, comprising a dowel and/or a lock screw or Allen screw suitable for interfering with said protuberance according to said first operative configuration or with a recessed seat present in a second projecting or tang portion of said at least one insert according to said second operative configuration, and an opening arranged on the side surface of said proximal portion of said humeral component, suitable for allowing the insertion of said dowel and/or a seat arranged on the side surface of said humeral component for the entry of said lock screw or Allen screw.

21. The prosthesis according to claim 20, wherein said dowel is made from a material suitable for interfering with or blocking said protuberance or said recessed seat or has a substantially threaded bolt-type configuration.

22. The prosthesis according to claim 20, wherein said opening is connected with said recess or notch.

23. A method for assembling a prosthesis for a shoulder joint according to a first operative configuration, said prosthesis comprising a humeral component equipped with a stem, a head component equipped with an axis of symmetry (S) and connection or articulation means of said humeral component with said head component, wherein said humeral component is suitable for being constrained to an end of the humerus bone close to the shoulder joint, wherein said humeral component comprises a proximal portion, wherein said stem is suitable for being inserted in use in the humerus of a patient and wherein said proximal portion is suitable for facing in use towards the glenoid cavity of the patient's shoulder, wherein said humeral component comprises a joining portion positioned between said stem and said proximal portion, wherein said humeral component comprises a single piece comprised of said stem, said proximal portion and said joining portion stably constrained to each other, the method comprising the steps of:

providing said humeral component comprising said proximal portion comprising a concave seat (C) and/or a configuration substantially cup-shaped, or hemi-spherical or half-spherical regular, irregular or incomplete that makes said concave seat (C) and/or a side or perimeter wall that defines said concave seat (C), wherein said proximal portion comprises a recess or notch formed within the joining portion and extending from a bottom of the concave seat of said humeral component according to a longitudinal axis (V) towards said stem, providing said head component comprising a protuberance that extends according to an axis of symmetry (Z2) from said head component, inserting said protuberance into said recess or notch, said concave seat (C) being suitable for at least partially containing said head component or articulating with said convex articulating surface of said head component, fixing said protuberance in said recess or notch, thus providing a connection between said head component and said humeral component, so that said head component can articulate during use with the glenoid cavity of the shoulder joint and so that said prosthesis has an anatomical configuration.

24. The method according to claim 23, wherein said step of fixing said protuberance into said recess or notch comprises the following steps:

pressure or interlockingly inserting or screwing said protuberance in said recess or notch, providing a dowel, providing said humeral component equipped with an opening arranged on the side surface of said proximal portion of said humeral component, and inserting said dowel into said opening so as to lock said protuberance in position in said recess or notch.

25. A method for assembling a prosthesis for a shoulder joint according to a second operative configuration, said prosthesis comprising a humeral component equipped with a stem, a head component and connection or articulation means of said humeral component with said head component, wherein said humeral component is suitable for being constrained to an end of the humerus bone close to the shoulder joint, wherein said humeral component comprises a proximal portion, wherein said stem is suitable for being inserted in use in the humerus of a patient and wherein said proximal portion is suitable for facing in use towards the glenoid cavity of the patient's shoulder, wherein said humeral component comprises a joining portion positioned between said stem and said proximal portion, wherein said humeral component comprises a single piece comprised of said stem, said proximal portion and said joining portion stably constrained to each other, the method comprising the steps of:

providing said humeral component comprising a proximal portion comprising a concave seat (C) and/or a configuration substantially cup-shaped, or hemi-spherical or half-spherical regular, irregular or incomplete that makes said concave seat (C) and/or a side or perimeter wall that defines said concave seat (C), wherein said proximal portion comprises a recess or notch formed within the joining portion and extending from a bottom of said concave seat (C) of said humeral component towards said stem, providing said head component comprising a protuberance that extends from said head component, and wherein said head component has a hemispherical or semispherical configuration determined by a convex surface and a base, wherein said convex surface substantially matches said concave seat (C), said concave seat (C) being suitable for at least partially articulating with said head component or articulating with said convex articulating surface of said head component, and inserting said convex surface of said head component in an articulated manner into said concave seat (C), thus providing articulation between said head component and said humeral component, so that said protuberance can be inserted during use in the glenoid cavity of the shoulder joint and so that said prosthesis has a reverse-type configuration.

26. The method according to claim 25, comprising the following steps:

providing at least one insert suitable for articulating with said head component, wherein said at least one insert has a first portion that is cup-shaped, or hemi-spherical shaped or half-sphere shaped regular, irregular or even incomplete and a second projecting or tang portion, and inserting said second projecting or tang portion into said recess or notch, fixing said second projecting or tang portion in said recess or notch.

27. The method according to claim 26, wherein said step of fixing said second projecting or tang portion in said recess or notch comprises the following steps:

pressure or interlockingly inserting or screwing said second projecting or tang portion in said recess or notch, providing a dowel, providing said humeral component equipped with an opening arranged on the side surface of said proximal portion of said humeral component, and inserting said dowel into said opening so as to lock said second projecting or tang portion in position in said recess or notch.

* * * * *